(12) United States Patent
Salvati et al.

(10) Patent No.: US 10,539,537 B2
(45) Date of Patent: Jan. 21, 2020

(54) THIN FILM BULK ACOUSTIC RESONATOR WITH SIGNAL ENHANCEMENT

(71) Applicant: QORVO US, INC., Greensboro, NC (US)

(72) Inventors: Michael Salvati, Minnetrista, MN (US); Ian Robert Harmon, Minneapolis, MN (US)

(73) Assignee: QORVO US, INC., Greensboro, NC (US)

( * ) Notice: Subject to any disclaimer, the term of this patent is extended or adjusted under 35 U.S.C. 154(b) by 0 days.

(21) Appl. No.: 16/285,304

(22) Filed: Feb. 26, 2019

(65) Prior Publication Data

US 2019/0187098 A1    Jun. 20, 2019

Related U.S. Application Data

(60) Division of application No. 14/850,353, filed on Sep. 10, 2015, now Pat. No. 10,234,425, which is a continuation of application No. PCT/US2014/027743, filed on Mar. 14, 2014.

(60) Provisional application No. 61/790,076, filed on Mar. 15, 2013, provisional application No. 62/050,589, filed on Sep. 15, 2014.

(51) Int. Cl.
*G01N 29/02*     (2006.01)
*G01N 33/543*    (2006.01)
*G01N 29/036*    (2006.01)

(52) U.S. Cl.
CPC ......... *G01N 29/022* (2013.01); *G01N 29/036* (2013.01); *G01N 33/54373* (2013.01); *G01N 2291/0255* (2013.01); *G01N 2291/0256* (2013.01); *G01N 2291/0426* (2013.01)

(58) Field of Classification Search
None
See application file for complete search history.

(56) References Cited

U.S. PATENT DOCUMENTS

| | | |
|---|---|---|
| 4,361,026 A | 11/1982 | Muller et al. |
| 4,654,127 A | 3/1987 | Baker et al. |
| 4,999,284 A | 3/1991 | Ward et al. |
| 5,404,628 A | 4/1995 | Ketcham |
| 5,405,510 A | 4/1995 | Betts et al. |
| 5,693,233 A | 12/1997 | Schembri |
| 5,821,833 A | 10/1998 | Lakin |
| 5,894,647 A | 4/1999 | Lakin |
| 5,922,591 A | 7/1999 | Anderson et al. |
| 5,932,953 A | 8/1999 | Drees et al. |

(Continued)

FOREIGN PATENT DOCUMENTS

| | | |
|---|---|---|
| CN | 1 566 933 A | 1/2005 |
| DE | 10 2005 052752 A1 | 5/2007 |

(Continued)

OTHER PUBLICATIONS

European Patent Application No. 14764974.3, filed Mar. 14, 2014; Extended European Search dated Oct. 10, 2016; 11 pages.

(Continued)

*Primary Examiner* — Robert T. Crow
(74) *Attorney, Agent, or Firm* — Mueting, Raasch & Gebhardt, P.A.

(57) ABSTRACT

Sensitivity of thin film bulk acoustic resonance (TFBAR) sensors is enhanced by mass amplification and operating a high frequency.

14 Claims, 7 Drawing Sheets

(56) References Cited

U.S. PATENT DOCUMENTS

| | | | |
|---|---|---|---|
| 5,936,150 A | 8/1999 | Kobrin et al. | |
| 5,942,958 A | 8/1999 | Lakin | |
| 6,107,721 A | 8/2000 | Lakin | |
| 6,114,635 A | 9/2000 | Lakin et al. | |
| 6,235,488 B1 | 5/2001 | Tom-May et al. | |
| 6,291,931 B1 | 9/2001 | Lakin | |
| 6,441,703 B1 | 8/2002 | Panasik | |
| 6,686,128 B1 | 2/2004 | Lakin et al. | |
| 6,720,844 B1 | 4/2004 | Lakin | |
| 7,241,421 B2 | 7/2007 | Webster et al. | |
| 7,288,229 B2 | 10/2007 | Turner et al. | |
| 7,353,695 B2 | 4/2008 | Fitch et al. | |
| 7,405,054 B1 | 7/2008 | Hasenbank et al. | |
| 7,419,821 B2 | 9/2008 | Davis et al. | |
| 7,468,138 B2 | 12/2008 | Weinberg et al. | |
| 7,666,687 B2 | 2/2010 | Webster et al. | |
| 7,695,681 B2 | 4/2010 | Wang et al. | |
| 7,963,151 B2 | 6/2011 | Godfrey et al. | |
| 8,040,494 B2 | 10/2011 | Ermantraut et al. | |
| 8,066,944 B2 | 11/2011 | Carter et al. | |
| 8,084,002 B2 | 12/2011 | Carter et al. | |
| 8,154,093 B2 | 4/2012 | Bradley et al. | |
| 8,309,039 B2 | 11/2012 | Webster et al. | |
| 8,309,364 B2 | 11/2012 | Miller et al. | |
| 8,409,875 B2 | 4/2013 | Johal et al. | |
| 8,467,039 B2 | 6/2013 | Ermantraut et al. | |
| 9,032,782 B1 | 5/2015 | Van Deusen et al. | |
| 10,234,425 B2 * | 3/2019 | Salvati | G01N 29/022 |
| 2001/0049148 A1 | 12/2001 | Wolk et al. | |
| 2004/0262162 A1 | 12/2004 | Roach et al. | |
| 2006/0054941 A1 | 3/2006 | Lu et al. | |
| 2006/0125489 A1 | 6/2006 | Feucht et al. | |
| 2006/0133953 A1 | 6/2006 | Zhang et al. | |
| 2006/0222568 A1 | 10/2006 | Wang et al. | |
| 2007/0120625 A1 | 5/2007 | Larson et al. | |
| 2007/0210349 A1 | 9/2007 | Lu et al. | |
| 2009/0017491 A1 | 1/2009 | Lemme et al. | |
| 2009/0059230 A1 | 3/2009 | Takada et al. | |
| 2009/0074951 A1 | 3/2009 | Bellew et al. | |
| 2009/0170119 A1 | 7/2009 | Lee et al. | |
| 2009/0282902 A1 | 11/2009 | Warthoe | |
| 2010/0105079 A1 | 4/2010 | Warthoe | |
| 2010/0127600 A1 | 5/2010 | Loschonsky et al. | |
| 2010/0189601 A1 | 7/2010 | Crawford et al. | |
| 2010/0218353 A1 | 9/2010 | Kolosov et al. | |
| 2010/0291668 A1 | 11/2010 | Bertrand et al. | |
| 2011/0008776 A1 | 1/2011 | Warthoe et al. | |
| 2011/0269249 A1 | 11/2011 | Warthoe et al. | |
| 2011/0316522 A1 | 12/2011 | Shinobu et al. | |
| 2012/0164753 A1 | 6/2012 | Johnston et al. | |
| 2012/0190128 A1 | 7/2012 | Nikbakht et al. | |
| 2012/0196384 A1 | 8/2012 | Zhang et al. | |
| 2012/0304776 A1 | 12/2012 | Novotny | |
| 2013/0224732 A1 | 8/2013 | Lee et al. | |
| 2014/0127826 A1 | 5/2014 | Johal et al. | |
| 2014/0154697 A1 | 6/2014 | Johal et al. | |
| 2015/0377834 A1 * | 12/2015 | Salvati | G01N 29/022 435/6.11 |
| 2016/0091506 A1 | 3/2016 | Webster | |

FOREIGN PATENT DOCUMENTS

| | | |
|---|---|---|
| JP | 05-503463 A | 6/1993 |
| JP | 2012-103002 A | 5/2012 |
| WO | WO 91/05261 A1 | 4/1991 |
| WO | WO 91/10497 A1 | 7/1991 |
| WO | WO 99/00855 | 1/1999 |
| WO | WO 2004/057319 A1 | 7/2004 |
| WO | WO 2008/019693 A2 | 2/2008 |
| WO | WO 2011/102065 A1 | 8/2011 |
| WO | WO 2012/054758 A2 | 4/2012 |
| WO | WO 2014/012136 A2 | 1/2014 |
| WO | WO 2014/143680 A1 | 9/2014 |
| WO | WO 2014/190240 A1 | 11/2014 |
| WO | WO 2014/190295 A2 | 11/2014 |
| WO | WO 2016/044055 A1 | 3/2016 |
| WO | WO 2016/044132 A1 | 3/2016 |

OTHER PUBLICATIONS

European Patent Application No. 15842191.7, filed Mar. 10, 2017; Extended European Search Report and Search Opinion dated Feb. 27, 2018; 10 pages.

Chen et al., "A pure shear mode ZnO film resonator for the detection of organophosphorous pesticides" Sensors and Actuators B: Chemical, Jun. 26, 2012; 171-172:1081-6.

Gan et al. "A Signal-Amplified Piezoelectric Sensor for the Detection of hs-CRP Using HRP Doped Magnetic Core-Shell Fe3O4@SiO2@Au Nanostructures as Labels," 2012, *Int. J. Electrochem. Sci.*, 7:11564-77.

International Patent Application No. PCT/US2014/027743, filed Mar. 14, 2014; International Search Report and Written Opinion dated Jul. 10, 2014; 11 pages.

International Patent Application No. PCT/US2014/027743, filed Mar. 14, 2014; I International Preliminary Report on Patentability dated Sep. 24, 2015; 8 pages.

International Patent Application No. PCT/US2015/049387, filed Sep. 10, 2015; International Search Report and Written Opinion dated Dec. 17, 2015; 3 pages.

International Patent Application No. PCT/US2015/049387, filed Sep. 10, 2015; I International Preliminary Report on Patentability dated Mar. 21, 2017; 8 pages.

Kokkonen et al., "Measurement of Evanescent Wave Properties of a Bulk Acoustic Wave Resonator" IEEE Transactions on Ultrasonics, Ferroelectrics, and Frequency Control, Mar. 2012; 59(3):557-59.

Lee et al. "Highly sensitive biosensing using arrays of plasmonic Au nanodisks realized by nanoimprint lithography," Feb. 22, 2012, *ACS Nano*, 5(2):897-904.

Martin et al., "Optimisation of the enzyme-based determination of hydrogen peroxide using the quartz crystal microbalance," Sep. 2002, *Biosensors and Bioelectronic*, 17(9):735-39.

Patolsky et al., "Precipitation of an insoluble produce on enzyme monolayer electrodes for biosensor applications: characterization by Faradaic impedance spectroscopy, cyclic voltammetry, and microgravimetric quartz crystal microbalance analyses," Aug. 1, 1999, *Anal. Chem.*, 71(15):3171-80.

Tang et al., "Enzymatically biocatalytic precipitates amplified antibody-antigen interaction for super low level immunoassay: an investigation combined surface plasmon resonance with electrochemistry," Dec. 15, 2007, *Biosensors and Bioelectronics*, 23(5):668-74.

Wang et al., "Label-free immunosensor based on micromachined bulk acoustic resonator for the detection of trace pesticide residues" Sensors and Actuators B: Chemical, Jan. 2014; 190:378-83. Epub Sep. 8, 2013.

Wingqvist et al., "Immunosensor utilizing a shear mode thin film bulk acoustic sensor" Sensors and Actuators B: Chemical, Oct. 20, 2007; 127(1):248-52.

U.S. Appl. No. 14/893,388, filed Nov. 23, 2015, Russell.

U.S. Appl. No. 16/503,720, filed Jul. 5, 2019, Webster et al.

European Patent Application No. 14801303.0, filed Dec. 18, 2015; Supplementary European Search Report and Search Opinion dated Nov. 22, 2016; 11 pages.

Waggoner et al., "Atomic Layer Deposited Silicon Dioxide Films on Nanomechanical Silicon Nitride Resonators" J Appl Phys, 2010; 107:114505. 5 pages.

Yang et al., "Effects of Diffusion Boundary Layer on Reaction Kinetics of Immunoassay in a Biosensor" J Appl Phys, Apr. 28, 2008; 10:084702. 10 pages.

\* cited by examiner

THIN FILM BULK ACOUSTIC RESONATOR WITH SIGNAL ENHANCEMENT

RELATED APPLICATIONS

This application is a divisional application of U.S. patent application Ser. No. 14/850,353, filed on Sep. 10, 2015, now U.S. Pat. No. 10,234,245 B2, which is a continuation of PCT Patent Application No. PCT/US2014/027743, filed on Mar. 14, 2014, which claims the benefit of U.S. Provisional Patent Application No. 61/790,076, filed on Mar. 15, 2013. This application also claims the benefit of U.S. Provisional Patent Application No. 62/050,589, filed on Sep. 15, 2014. The above-referenced applications are hereby incorporated herein by reference in their respective entireties to the extent that they do not conflict with the present disclosure.

FIELD

This disclosure generally relates to, among other things, signal enhancement of thin film bulk acoustic resonators (TFBARs) through amplification element mediated mass loading.

BACKGROUND

Piezoelectric devices such as thin film bulk acoustic resonators (TFBARs) and similar technologies like quartz crystal microbalances (QCM) have been employed as mass detectors for some time. One application of piezoelectric resonators is in detecting very small quantities of materials. Piezoelectric resonators used as sensors in such applications are sometimes called "micro-balances." A piezoelectric resonator is typically constructed as a thin, planar layer of crystalline or polycrystalline piezoelectric material sandwiched between two electrode layers. When used as a sensor, the resonator is exposed to the material being detected to allow the material to bind on a surface of the resonator.

One conventional way of detecting the amount of the material bound on the surface of a sensing resonator is to operate the resonator as an oscillator at its resonant frequency. As the material being detected binds on the resonator surface, the oscillation frequency of the resonator is reduced. The change in the oscillation frequency of the resonator, presumably caused by the binding of the material on the resonator surface, is measured and used to calculate the amount of the material bound on the resonator or the rate at which the material accumulates on the resonator surface.

The sensitivity of a piezoelectric resonator in air as a material sensor is theoretically proportional to the square of the resonance frequency. Thus, the sensitivities of material sensors based on the popular quartz crystal resonators are limited by their relatively low oscillating frequencies, which typically range from several MHz to about 100 MHz. The development of thin-film resonator (TFR) technology can potentially produce sensors with significantly improved sensitivities. A thin-film resonator is formed by depositing a thin film of piezoelectric material, such as AlN or ZnO, on a substrate. Due to the small thickness of the piezoelectric layer in a thin-film resonator, which is on the order of several microns, the resonant frequency of the thin-film resonator is on the order of 1 GHz. The high resonant frequencies and the corresponding high sensitivities make thin-film resonators useful for material sensing applications. However, mass sensitivity of even thin-film resonators may be limited for detection of certain analytes, such as biological analytes.

The use of piezoelectric resonator sensors in immunoassays has been described previously. In general piezoelectric based immunoassays, in which mass change is attributable to the immunological reaction between an antigen and an antibody, can in circumstances suffer from poor sensitivity and poor detection limit. Consequently, there is a need in the art for a piezoelectric-based specific binding assay in which the reaction between a molecular recognition component and its target analyte can be amplified to provide a more sensitive assay.

One such example is presented in U.S. Pat. No. 4,999,284 issued to Ward on 12 Mar. 1991, which discloses a method using a quartz crystal microbalance assay, in which the binding of analyte to a surface on or near a quartz crystal microbalance (QCM) is detected by a conjugate that includes an enzyme. The enzyme is capable of catalyzing the conversion of a substrate to a product capable of accumulating on or reacting with a surface of the QCM leading to a mass change and, hence, a change in resonant frequency.

SUMMARY

This disclosure describes, among other things, signal amplification to enhance sensitivity of TFBAR operating at a high frequency.

In embodiments, a method for detecting an analyte in a sample includes contacting an analyte or an analyte and a tag-linked analyte molecule, a first recognition component, and a signal amplification element-linked second recognition component to generate a complex comprising the first recognition component and the signal amplification element-linked second recognition component. The first recognition component is immobilized relative to a surface of a thin film bulk acoustic resonator (TFBAR) and is configured to selectively bind one or more of the analyte, the analyte molecule to which the tag is linked or the tag, or any of these molecules that are bound to the second recognition component. The signal amplification element-linked second recognition component is configured to selectively bind one or more of the analyte, the analyte molecule to which the tag is linked, or the tag, or any of these molecules that are bound to the first recognition component, or a combination thereof. The method further includes contacting the linked signal amplification element with one or more amplification precursors under conditions to convert the precursors into amplification molecules that add mass at a surface of the TFBAR. The added mass may result from deposition of the amplification molecule on the surface; binding of the amplification molecule to one or more of the analyte, the tag-linked analyte molecule, the first recognition component or the amplification element-linked second recognition component; or the like. The method also includes obtaining a measure related to the mass (e.g, mass of analyte, signal amplification element-linked second recognition component, and amplification molecule) added at the surface of the TFBAR.

The analyte or the analyte and the tag-linked analyte molecule, the first recognition component and the signal amplification element-linked second recognition component may be contacted in any suitable order. For example, the analyte or the analyte and the tag-linked analyte molecule may be contacted with the signal amplification element-linked second recognition component prior to contact with the first recognition component immobilized relative to the surface of the TFBAR. By way of further example, the analyte or the analyte and the tag-linked analyte molecule may be contacted with the first recognition component prior to contact with the signal amplification element-linked second recognition component. By way of yet another example, the analyte or the tag-linked analyte molecule, the first recognition component and the signal amplification element-linked second recognition component may be contacted simultaneously.

The signal amplification element may be linked to second recognition component at any suitable time. In some embodiments, the signal amplification element is linked to the second recognition component prior to contact with the analyte or the tag-linked analyte molecule. In some embodiments, the signal amplification element is linked to the secondary recognition component after the second recognition component is contacted with the analyte or the tag-linked analyte. In some embodiments, the signal amplification element is linked to the second recognition component by a covalent bond. In some embodiments, the signal amplification element and the second recognition component include moieties that bind with high affinity. By way of example, the secondary recognition component can be biotinylated, and the signal amplification element may be conjugated to avidin or streptavidin; or vice-versa.

The mass added at the surface of the TFBAR may be measured by any suitable process. In embodiments, the mass is measured by: (i) coupling an input electrical signal to the TFBAR, the input electric signal having a phase and having a frequency within a resonance band of the piezoelectric resonator, wherein the frequency is about 500 MHz or greater (such as about 700 MHz or greater, about 800 MHZ or greater, about 900 MHz or greater, about 1 GHz or greater, about 1.2 GHZ or greater, about 1.4 GHZ or greater, about 1.5 GHZ or greater, 1.8 GHZ or greater, about 2 GHz or greater, about 2.2 GHz or greater, about 2.4 GHz or greater, about 2.5 GHz or greater, from about 500 MHz to about 4 GHz, from about 800 MHz to about 3 GHz, from about 800 MHz to about 10 GHz, or from about 2 GHz to about 2.5 GHz); (ii) transmitting the input electrical signal through the TFBAR to generate an output electrical signal having a frequency and a phase; (iii) receiving the output electrical signal from the TFBAR; and (iv) determining a change in frequency or phase of the output electrical signal caused by the added mass at the surface of the TFBAR, wherein the change in frequency of phase serves as a measure of the mass added at the surface of the TFBAR.

One or more embodiments of the apparatuses, systems or methods described herein provide one or more advantages over prior sensors, devices, systems or methods for detecting small quantities of an analyte. As described herein, at higher frequencies larger TFBAR signal amplification was surprisingly observed with amplification element-mediated mass loading than at lower frequencies. Accordingly, advantages of higher frequencies appear to be even further enhanced when employed in combination with signal amplification. This and other advantages will be readily understood by those of skill in the art from the following detailed description.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description several specific embodiments of compounds, compositions, products and methods are disclosed. It is to be understood that other embodiments are contemplated and may be made without departing from the scope or spirit of the present disclosure. The following detailed description, therefore, is not to be taken in a limiting sense.

This disclosure generally relates to, among other things, methods, devices, sensors and systems for detecting an analyte. The method, devices, sensors and systems use a thin film bulk acoustic resonator (TFBAR) that measures a change in frequency or phase of the resonator caused by the binding of the analyte on a surface of the resonator. The binding signal is enhanced through amplification element-mediated mass loading. An input electrical signal having a phase and having a frequency within a resonance band of the piezoelectric resonator, which in the case of some embodiments of the present disclosure may be about 500 MHz or greater, such as about 1.5 GHz or greater, is coupled to and transmitted through the resonator to generate an output electrical signal which is frequency-shifted or phase-shifted from the input signal due to binding, deposition, etc. of material being detected on the resonator surface and amplification due to the amplification element-mediated mass loading. The output electrical signal received from the piezoelectric resonator is analyzed to determine the change in frequency or phase caused by the binding of analyte and amplification element mediated mass deposition on the resonator surface. The measured change in frequency or phase provides quantitative information regarding the analyte (or tag-linked analyte molecule) bound to the resonator surface.

Sensors, Devices and Systems

The sensors disclosed herein include at least one thin film resonator sensor, such as a thin film bulk acoustic resonator (TFBAR) sensor. A TFBAR sensor includes a piezoelectric layer, or piezoelectric substrate, and input and output transducer. TFBAR sensors are small sensors making the technology suitable for use in handheld devices. Accordingly, a handheld device for detecting target analytes comprising a sensor described herein is contemplated.

Figure 1A:
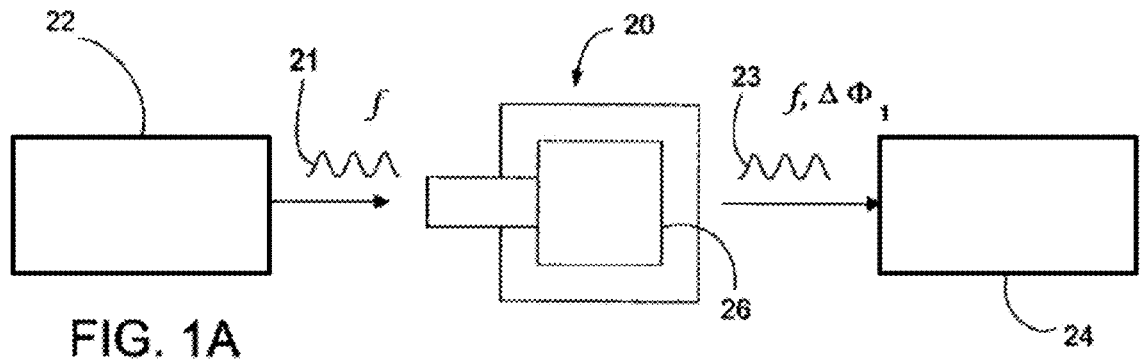
FIGS. 1A-1C are schematic diagrams illustrating the operational principles of embodiments of thin film bulk acoustic resonator (TFBAR) sensing devices.
Figure 1B:
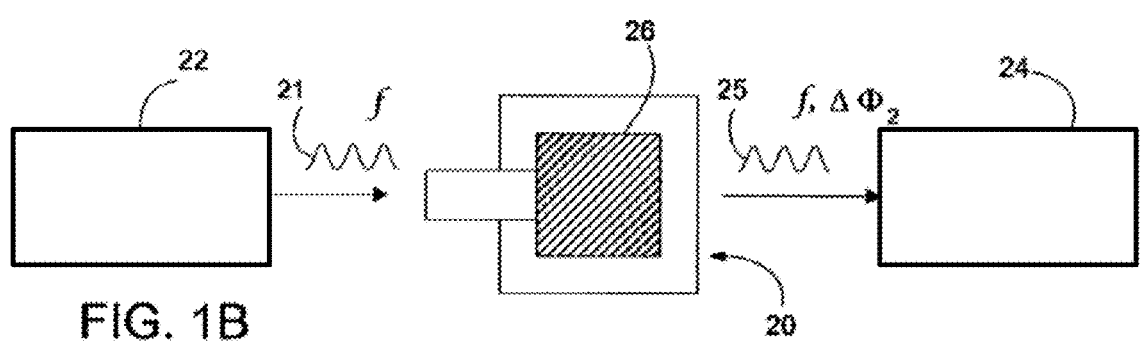

Turning now to the drawings with reference to FIGS. 1A and 1B, general operating principles of an embodiment of a bulk-acoustic wave piezoelectric resonator 20 used as a sensor to detect an analyte are shown. The resonator 20 typically includes a planar layer of piezoelectric material bounded on opposite sides by two respective metal layers which form the electrodes of the resonator. The two surfaces of the resonator are free to undergo vibrational movement when the resonator is driven by a signal within the resonance band of the resonator. When the resonator is used as a sensor, at least one of its surfaces is adapted to provide binding sites for the material being detected. The binding of the material on the surface of the resonator alters the resonant characteristics of the resonator, and the changes in the resonant characteristics are detected and interpreted to provide quantitative information regarding the material being detected.

By way of example, such quantitative information may be obtained by detecting a change in the insertion or reflection coefficient phase shift of the resonator caused by the binding of the material being detected on the surface of the resonator. Such sensors differ from those that operate the resonator as an oscillator and monitor changes in the oscillation frequency. Rather such sensors insert the resonator in the path of a signal of a pre-selected frequency and monitor the variation of the insertion or reflection coefficient phase shift caused by the binding of the material being detected on the resonator surface. Of course, sensors that monitor changes in oscillation frequency may also be employed in accordance with signal amplification described herein.

In more detail, FIG. 1A shows the resonator 20 before the material being detected is bound to its surface 26. The depicted resonator 20 is electrically coupled to a signal source 22, which provides an input electrical signal 21 having a frequency f within the resonance band of the resonator. The input electrical signal is coupled to the resonator 20 and transmitted through the resonator to provide an output electrical signal 23. In the depicted embodiment, the output electrical signal 23 is at the same frequency as the input signal 21, but differs in phase from the input signal by a phase shift $\Delta\Phi_1$, which depends on the piezoelectric properties and physical dimensions of the resonator. The output signal 23 is coupled to a phase detector 24 which provides a phase signal related to the insertion phase shift.

FIG. 1B shows the sensing resonator 20 with the material being detected bound on its surface 26. The same input signal is coupled to the resonator 20. Because the resonant characteristics of the resonator are altered by the binding of the material as a perturbation, the insertion phase shift of the output signal 25 is changed to $\Delta\Phi_2$. The change in insertion phase shift caused by the binding of the material is detected by the phase detector 24. The measured phase shift change is related to the amount of the material bound on the surface of the resonator.

Figure 1C:
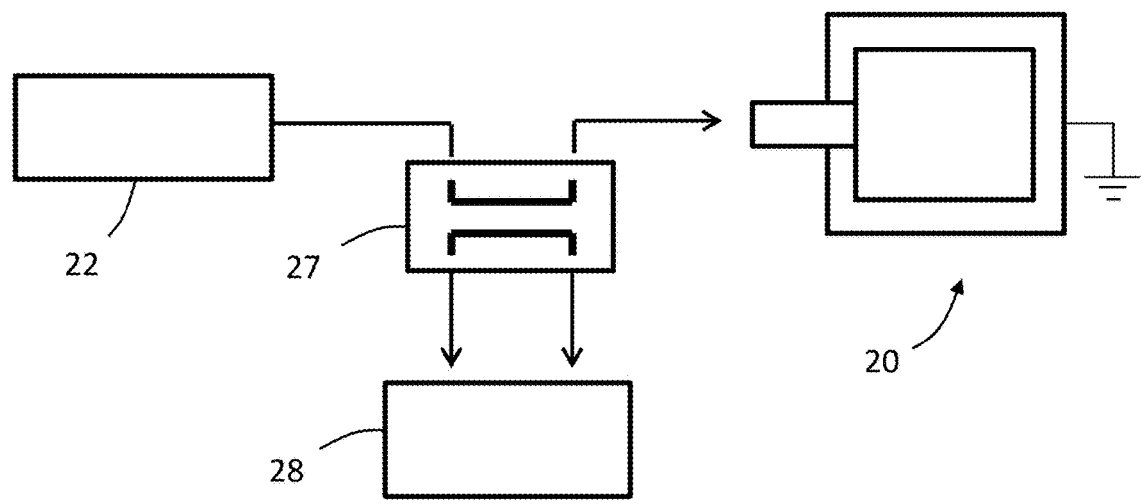

FIG. 1C shows an alternative to measuring the insertion phase of the resonator. A directional coupler 27 is added between the signal source 22 and the resonator 20 with the opposite electrode grounded. A phase detector 28 is configured to measure the phase shift of the reflection coefficient as a result of material binding to the resonator surface.

Other TFBAR phase-shift sensors that may be employed with the signal amplification aspects described herein include those described in, for example, U.S. Pat. No. 8,409,875 entitled "RESONATOR OPERATING FREQUENCY OPTIMIZATION FOR PHASE-SHIFT DETECTION SENSORS," which patent is hereby incorporated herein by reference in its entirety to the extent that it does not conflict with the disclosure presented herein. For example, sensor apparatuses may include (i) a sensing resonator comprising binding sites for an analyte; (ii) actuation circuitry configured to drive the sensing resonator in an oscillating motion; (iii) measurement circuitry arranged to be coupled to the sensing resonator and configured to measure one or more resonator output signals representing resonance characteristics of the oscillating motion of the sensing resonator; and (iv) a controller operatively coupled with the actuation and measurement circuitry. The controller can be interfaced with data storage containing instructions that, when executed, cause the controller to adjust the frequency at which the actuation circuitry drives the sensing resonator to maintain a resonance point of the sensing resonator. Accordingly, sensing may be accomplished by actuating the TFBAR into an oscillating motion; measuring one or more resonator output signals representing resonance characteristics of the oscillating motion of the TFBAR; and adjusting the actuation frequency of the sensing resonator to maintain a resonance point of the TFBAR. In embodiments, the frequency at which the actuation circuitry drives the sensing resonator is a frequency of maximum group delay.

Such phase detection approaches can be advantageously used with piezoelectric resonators of different resonant frequencies.

In various embodiments, TFBARs for use with the methods, devices, and system described herein have resonance frequencies of about 500 MHz or greater, such as about 700 MHz or greater, about 900 MHz or greater, about 1 MHz or greater, 1.5 GHz or greater, about 1.8 GH or greater, about 2 GHz or greater, 2.2 GHz or greater, 2.5 GHz or greater, about 3 GHZ or greater, or about 5 GHZ or greater can provide enhanced sensitivity when used with amplification element mediated mass loaded, which is described in more detail below. In embodiments, the TFBARs have resonance frequencies of from about 500 MHz to about 5 GHz, such as from about 900 MHz to about 3 GHz, or from about 1.5 GHz to about 2.5 GHz. Some of such frequencies are substantially higher than frequencies of previously described piezoelectric resonators.

The sensing resonators described herein are thin-film resonators. Thin film resonators comprise a thin layer of piezoelectric material deposited on a substrate, rather than using, for example, AT-cut quartz. The piezoelectric films typically have a thickness of less than about 5 micrometers, such as less than about 2 micrometers, and may have thicknesses of less than about 100 nanometers. Thin-film resonators are generally preferred because of their high resonance frequencies and the theoretically higher sensitivities. Depending on the applications, a thin-film resonator used as the sensing element may be formed to support either longitudinal or shear bulk-acoustic wave resonant modes. Preferably, the sensing element is formed to support shear bulk-acoustic wave resonant modes, as they are more suitable for use in a liquid sample.

Additional details regarding sensor devices and systems that may employ TFRs are described in, for example, U.S. Pat. No. 5,932,953 issued Aug. 3, 1999 to Drees et al., which patent is hereby incorporated herein by reference in its entirety to the extent that it does not conflict with the disclosure presented herein.

TFR sensors may be made in any suitable manner and of any suitable material. By way of example, a resonator may include a substrate such as a silicon wafer or sapphire, a Bragg mirror layer or other suitable acoustic isolation means, a bottom electrode, a piezoelectric material, and a top electrode.

Any suitable piezoelectric material may be used in a TFR. Examples of suitable piezoelectric substrates include lithium tantalate (LiTaO$_3$), lithium niobate (LiNbO$_3$), Zinc Oxide (ZnO), aluminum nitride (AlN), plumbum zirconate titanate (PZT) and the like.

Electrodes may be formed of any suitable material, such as aluminum, tungsten, gold, titanium, molybdenum, or the like. Electrodes may be deposited by vapor deposition or may be formed by any other suitable process.

Any suitable device or system may employ a thin film resonator and amplification as described herein. By way of example and with reference to FIG. 2, a system for detecting an analyte may include a container 10 (or more than one container), the thin film resonator 20, actuation circuitry 22, measurement circuitry 29, and control electronics 30. A fluid path couples the one or more containers 10 to the resonator 20. The control electronics 30 are operably coupled to the actuation circuitry and the measurement circuitry. In embodiments, control electronics 30 are configured to modify the frequency at which the actuation circuitry 22 oscillates the resonator 20 based on input from the measurement circuitry 29.

Figure 2:
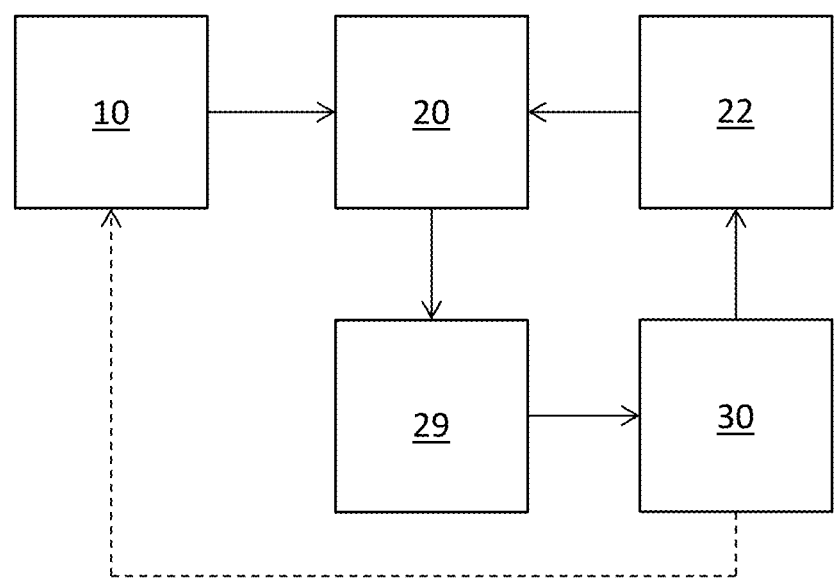
FIG. 2 is a schematic diagram showing components of a TFBAR system for detecting an analyte.

Still with reference to FIG. 2, the container 10 (or more than one container) may house an amplification molecule, an amplification element-linked second recognition component or components thereof, and optionally one or more of a tag, an analyte molecule, and a first recognition component. Each of these reagents is described in more detail below. Control electronics 30 may control the flow of such reagents from container 10 to resonator 20; e.g. via a pump, vacuum, or the like.

Any suitable control electronics 30 may be employed. For example, control electronics may include a processor, controller, memory, or the like. Memory may include computer-readable instructions that, when executed by processor or controller cause the device and control electronics to perform various functions attributed to device and control electronics described herein. Memory may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Control electronics 30 may include any one or more of a microprocessor, a controller, a digital signal processor (DSP), an application specific integrated circuit (ASIC), a field-programmable gate array (FPGA), or equivalent discrete or integrated logic circuitry. In some examples, control electronics 30 may include multiple components, such as any combination of one or more microprocessors, one or more controllers, one or more DSPs, one or more ASICs, or one or more FPGAs, as well as other discrete or integrated logic circuitry. The functions attributed to control electronics herein may be embodied as software, firmware, hardware or any combination thereof.

Molecular Recognition and Signal Amplification

Molecular recognition of a sample comprising a significant background signal may be facilitated by amplification of the signal. The sensors, systems and methods described herein employ a second recognition component comprising an amplification element such as a linked enzyme. The TFBAR sensors, at the higher frequency ranges described herein, responded very efficiently to mass increase of the sensor surface due to precipitation of a substrate cleaved by an enzyme.

Figure 3A:
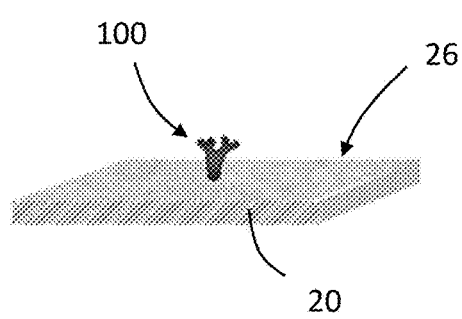
FIGS. 3A-D are schematic drawings illustrating an embodiment of signal amplification on a surface of a thin film resonator (TFR).
Figure 3B:
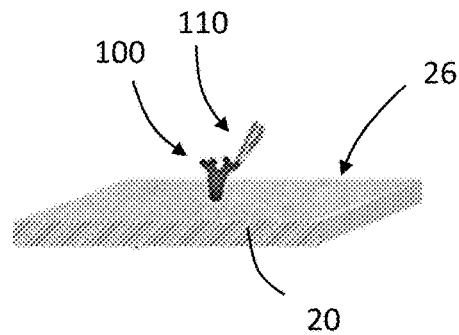
Figure 3C:
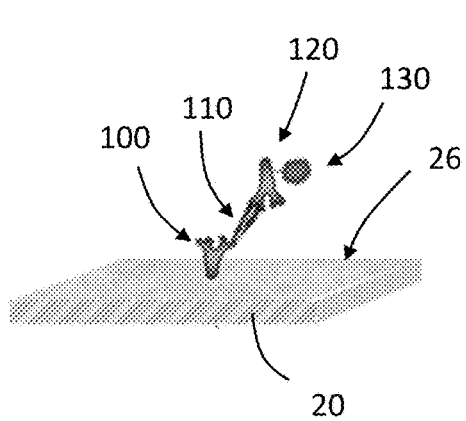
Figure 3D:
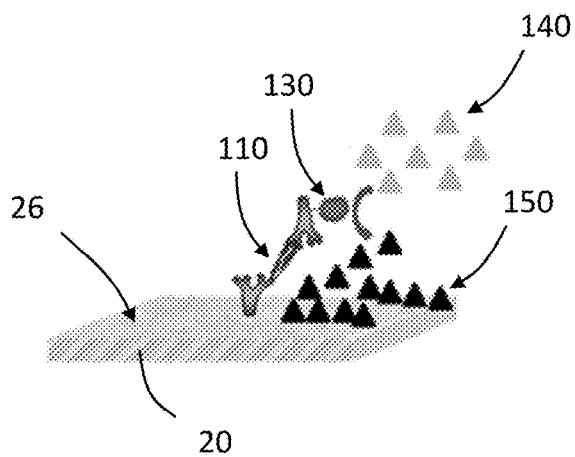

Referring now to FIGS. 3A-D, schematic drawings illustration enzyme amplification on a TFBAR are shown. As depicted in FIG. 3A, a molecular recognition component 100 configured to bind to an analyte is immobilized on a surface 26 of a resonator 20. The resonator 20 having immobilized molecular recognition component 100 may be contacted with a composition comprising an analyte 110, which may bind molecular recognition component 100 (see FIG. 3B). The resonator 20 having immobilized molecular recognition component 100 to which analyte 110 is bound may be contacted with a composition comprising a second molecular recognition component 120 linked to an amplification element 130 such as an enzyme. The second molecular recognition component 120 is configured to bind to analyte 110 such that the second molecular recognition component 120 and linked amplification element 130 are immobilized relative to the surface 26 (see FIG. 3C). In the depicted embodiments, a soluble substrate 140 may be converted by amplification element 130 to an insoluble product 150, which precipitates and accumulates on the surface 26 of the sensor 20, thereby amplifying the mass signal as a function of amount or concentration of bound analyte 110 (see FIG. 3D).

It will be understood that the series of events depicted in FIGS. 3A-3D are shown for purposes of illustration and that any other suitable sequence of events may be employed. For example, the analyte 110 may be contacted with the second molecular recognition component 120 (and bound amplification element 130) before the analyte (with bound second molecular recognition component) is contacted to the surface 26 of the resonator 20 relative to which the molecular recognition component 100 is immobilized. The substrate 140 may be present at the time the second molecular recognition component 120-amplification element 130 is added or may be added later. In any case, washing may be performed prior to amplification.

Non-limiting examples of target analytes include nucleic acids, proteins, peptides, antibodies, enzymes, carbohydrates, chemical compounds, or infectious species such as bacteria, fungi, protozoa, viruses and the like. In certain applications, the target analyte is capable of binding more than one molecular recognition component.

Any suitable molecular recognition component (e.g., 100 in FIG. 3) may be bound to the surface of a resonator. The molecular recognition component preferably selectively binds to the analyte of interest. By way of example, the molecular recognition component may be selected from the group consisting of nucleic acids, nucleotide, nucleoside, nucleic acids analogues such as PNA and LNA molecules, proteins, peptides, antibodies including IgA, IgG, IgM, IgE, lectins, enzymes, enzymes cofactors, enzyme substrates, enzymes inhibitors, receptors, ligands, kinases, Protein A, Poly U, Poly A, Poly lysine, triazine dye, boronic acid, thiol, heparin, polysaccharides, coomassie blue, azure A, metal-binding peptides, sugar, carbohydrate, chelating agents, prokaryotic cells and eukaryotic cells.

Any suitable method for immobilizing a molecular recognition component on a surface of a TFBAR may be used. By way of example, a uniform coating of epoxy silane may be deposited on the sensor surface using a vapor deposition process. Test and reference molecular recognition components, such as antibodies, may then be deposited onto the test and reference resonators using, for example, piezo based nanodispensing technology. Primary amines on the antibodies react with the epoxide groups covalently binding the antibody to the sensor surface. By way of further example, a thiol group, if present, of the molecular recognition component bind to a surface of the TFBAR. The surface of the TFBAR may be modified, as appropriate or necessary, to permit binding of the molecular recognition component.

Any suitable molecular recognition components, such as those described above, may be used as the second molecular recognition component (e.g., 120 in FIG. 3). The second molecular recognition component may be linked to any suitable amplification element, such as an enzyme. Preferably, the second molecular recognition component is an antibody and the amplification element is an enzyme.

Any suitable amplification element may be linked to the second molecular recognition component. In embodiments, the amplification element is an activatable polymerization initiator, such as a photoinitiator, a chemical initiator, or a thermoinitiator. The polymerization initiator may be activated in the presence of one or more monomers to cause a polymer to graft from the second molecular recognition component. In embodiments, the amplification element is an enzyme. In embodiments, the enzyme is capable of converting a substrate that is soluble in the assay environment to an insoluble product that precipitates on the surface of the sensor. Examples of suitable enzymes include alkaline phosphatase (ALP), horse radish peroxidase (HRP), beta galactosidase, and glucose oxidase.

Examples of enzyme/substrate systems that are capable of producing an insoluble product which is capable of accumulating on a surface of a TFBAR include alkaline phosphatase and 5-bromo-4-chloro-3-indolylphosphate/nitroblue tetrazolium chloride (BCIP/NBT). The enzymatically catalyzed hydrolysis of BCIP produces an insoluble dimer, which may precipitate on the surface of the sensors. Other analogous substrates having the phosphate moiety replaced with such hydrolytically cleavable functionalities as galactose, glucose, fatty acids, fatty acid esters and amino acids can be used with their complementary enzymes. Other enzyme/substrate systems include peroxidase enzymes, for example horse radish peroxidase (HRP) or myeloperoxidase, and one of the following: benzidene, benzidene dihydrochloride, diaminobenzidene, o-tolidene, o-dianisidine and tetramethyl-benzidene, carbazoles, particularly 3-amino-9-ethylcarbazole, and various phenolic compounds all of which have been reported to form precipitates upon reaction with peroxidases. Also, oxidases such as alphahydroxy acid oxidase, aldehyde oxidase, glucose oxidase, L-amino acid oxidase and xanthine oxidase can be used with oxidizable substrate systems such as a phenazine methosulfate-nitriblue tetrazolium mixture.

It will be understood that any type of competition assay may be employed. It will be further understood that the analyte may be modified to include a tag recognizable by the first or second recognition complex, such as a streptavidin tag; biotin tag; a chitin binding protein tag; a maltose binding protein tag; a glutathione-S-transferase tag; a poly (His) tag; an epitope tag such as a Myc tag, a HA tag, or a V5 tag; or the like. It will be further understood that the tag-linked analyte may include a variant or derivative of the analyte. The variant or derivative is a variant or derivative that is selectively recognizable by the first or second molecular recognition component that is configured to recognize the analyte. In some situations, it may be desirable that the variant or derivative analyte have an affinity for the first or second molecular recognition component that is different than the affinity of the non-tag-linked analyte. The variant or derivative of the analyte may be a variant or derivative that allows for ease of manufacture of the tag-linked analyte. For example, the tag-linked analyte may comprise a recombinant polypeptide, etc.

When competition assays employing tag-linked analyte molecules are performed, the tag-linked analyte molecule, rather than or in addition to the analyte, may bind a first molecular recognition component immobilized on a surface of a resonator.

Referring now to FIG. 4, an embodiment of a signal amplification assay is depicted. Many of the components of FIG. 4 are the same or similar to the components depicted in FIG. 3. If a particular element is not specifically discussed with regard to FIG. 4, reference is made to the numbered element in FIG. 3 above. A signal amplification element 130 may be linked to second recognition component 120 at any suitable time. In some embodiments (not depicted in FIG. 4), the signal amplification element 130 is linked to the second recognition component 120 prior to contact with the analyte 110 or the tag-linked analyte molecule. In some of such embodiments, the signal amplification element 130 is covalently bound to the second recognition component 120.

Figure 4A:
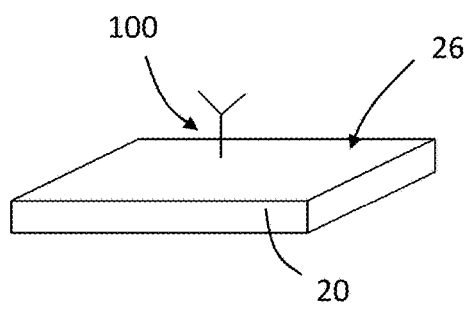
FIGS. 4A-D are schematic drawings illustrating an embodiment of signal amplification on a surface of a TFR.
Figure 4B:
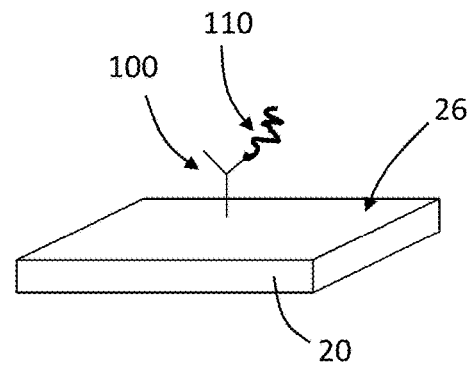
Figure 4C:
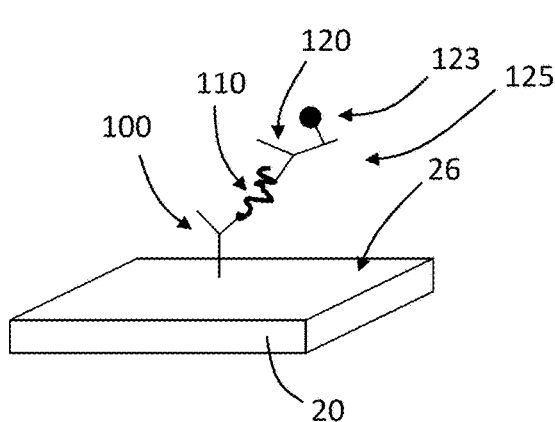
Figure 4D:
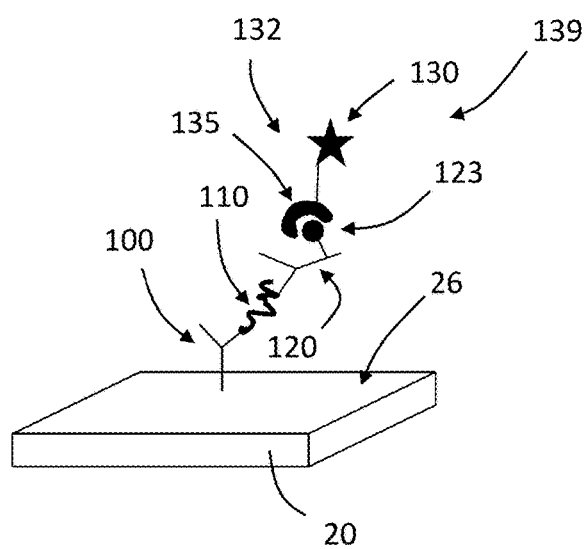

In some embodiments (e.g., as depicted in FIGS. 4C-D), signal amplification element 130 is linked to secondary recognition component 120 after second recognition component 120 is contacted with the analyte 110 or the tag-linked analyte. By way of example, second recognition component 120 can include first binding partner 123 configured to selectively bind second binding partner of signal amplification element 130. First binding partner 123 is preferably covalently bound to second recognition component 120. Second binding partner 135 is preferably covalently bound to signal amplification element 130. First 123 and second 135 binding partners preferably bind with high affinity.

Any suitable combination of first 123 and second 135 binding partners may be employed. By way of example, secondary recognition component 120 can be biotinylated, and signal amplification element 130 may be conjugated to streptavidin; or vice-versa. By way of further example, one of first and second binding partners can be a polyhistidine (His) tag, and the other of first and second binding partners can be, for example, a nickel or copper chelator, such as iminodiacetic acid (Ni-IDA) and nitrilotriacetic acid (Ni-NTA) for nickel and carboxylmethylaspartate (Co-CMA) for cobalt, which the poly(His) tag can bind with micromolar affinity. Generally nickel-based resins have higher binding capacity, while cobalt-based resins offer the highest purity. By way of yet another example, one of first and second binding partners can be a glutathione-S-transferase (GST) tag, and the other of first and second binding partners can be glutathione. For yet another example, one of first and second binding partners can be a maltose binding protein tag, and the other of first and second binding partners can be amylose or maltose. As another example, one of first and second binding partners can be a chitin binding protein tag, and the other of first and second binding partners can be chitin. It will be understood that above-presented binding partners are merely examples of high affinity binding partners that may be conjugated to a second recognition component or a signal amplification element and that other binding partners are contemplated herein. Further, it will be understood that more than one set of binding partners may be employed to link second recognition component to signal amplification element.

Binding partners may be conjugated to second recognition component or signal amplification element through any suitable technique. For example, chemical conjugation or recombinant techniques may be employed to link a binding partner to second recognition component or signal amplification element, as appropriate. Such techniques are well known to those of skill in the art. For example, a heterobifunctional cross linker utilizing NHS-ester and maleimide functional groups may be employed as known to those of skill in the art.

It will be understood that, if signal amplification element and second recognition component include complementary binding partners, the signal amplification element may be linked to second recognition component via binding partners at any suitable time. For example and as shown in FIGS. 4C-D, signal amplification element 130 may be linked to second recognition component 120 after second recognition component 120 is contacted with analyte 110 or tag-linked analyte. In some embodiments, signal amplification element 130 containing second binding partner 135 is contacted with second recognition component 120 containing first binding partner 123 before second recognition component 120 is contacted with analyte 110 or tag-linked analyte or at the same time as second recognition component 120 is introduced to resonator.

Figure 5A:
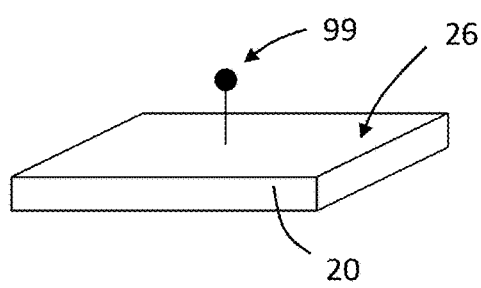
FIGS. 5A-B are schematic diagrams of an embodiment of a first binding partner bound to a surface of a TFR (5A) and a recognition component bound to a second binding partner, which is bound to the first binding partner (5B).
Figure 5B:
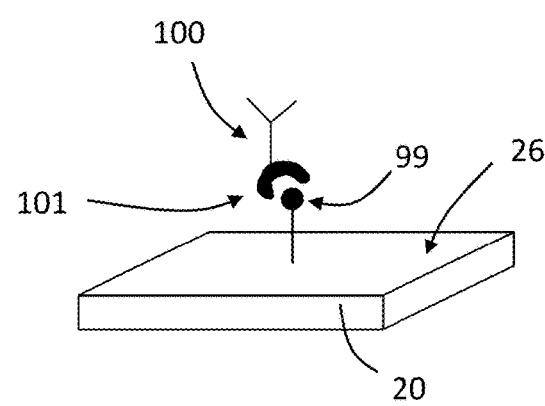
Figure 6A:
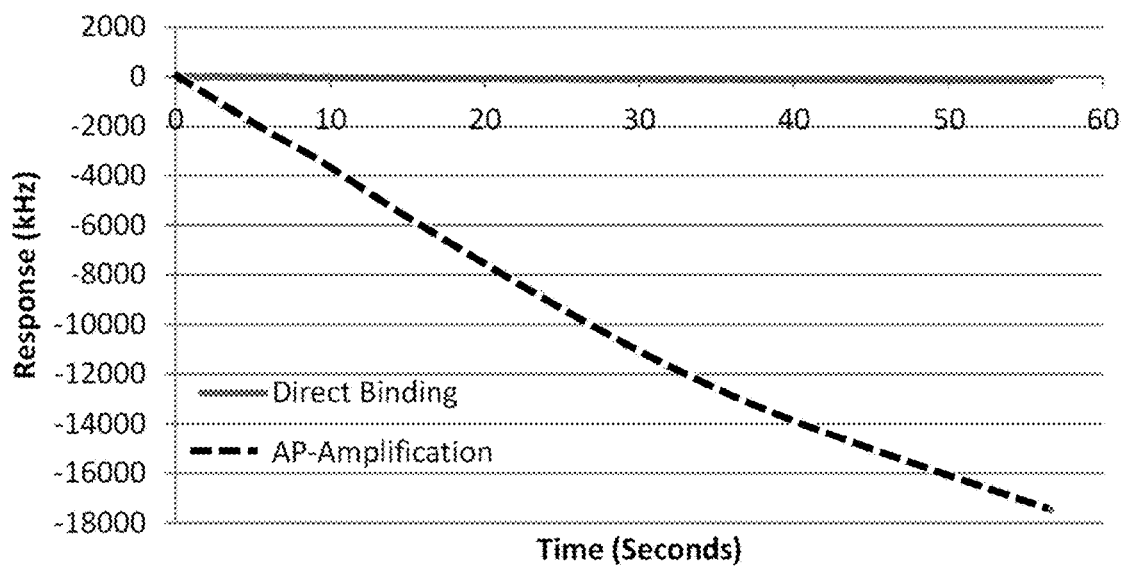
FIG. 6A is a plot of response over time of direct analyte binding and enzyme amplified analyte binding on and embodiment of a TFBAR.
Figure 6B:
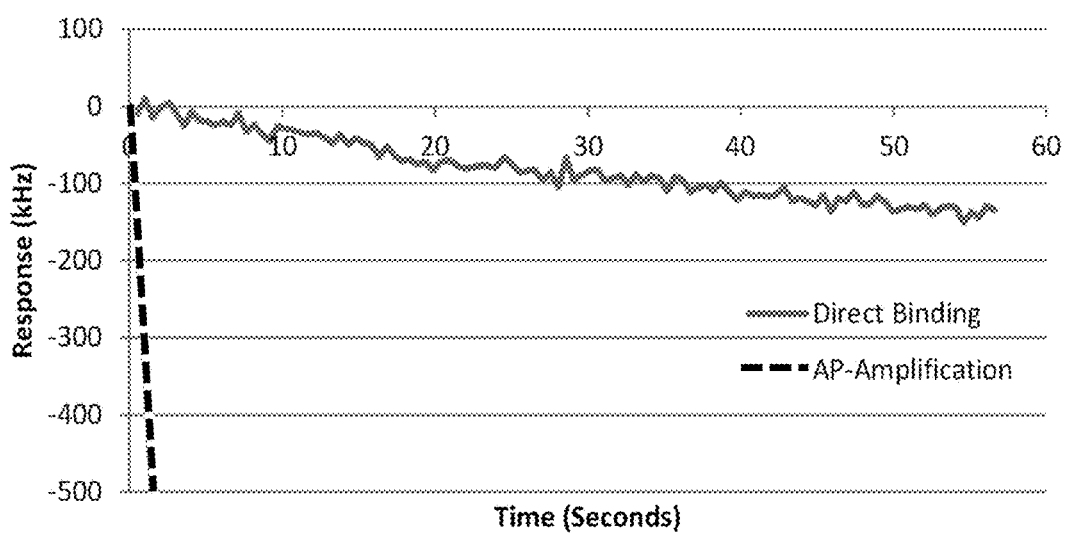
FIG. 6B is a plot showing details of a portion of the plot presented in FIG. 4A.

Referring now to FIGS. 5A-B, a first molecular recognition component 100 may be bound to a surface 26 of a TFBAR 20 via one or more intermediate. For example, a first binding partner 99 may be bound to the surface 26 and the first molecular recognition component 100 may include a second binding partner 101 configured to selectively bind to the first binding partner 99. The binding partners 99, 101 may be binding partners as described above (e.g., with regard to FIG. 4). First recognition component 100 may be bound to surface 26 via binding partners 99, 101 at any suitable time, such as before the sensor 20 is incorporated into a device or system or after the sensor 20 is incorporated into the device or system. For example, first recognition component 100 may be bound to surface 26 via binding partners 99, 101 as a first step of, or during, an analyte detection assay.

Amplification Element-Mediated Mass Loading/Signal Amplification with TFBARs

It has been noted that, as resonance frequency increases, sensitivity for mass detection should also increase. However, this is not always observed in practice. In theory, a TFBAR having a resonance frequency to about 2.2 GHz should afford sufficient sensitivity to detect low concentrations of analytes without the use of signal amplification/mass-loading as described herein. However, the inventors found that even with such high resonance frequencies, TFBAR sensors were not sufficiently sensitive to detect low levels of analyte. However, by utilizing the amplification/mass-loading techniques described herein, more of the theoretical gains in sensitivity offered by operating at higher frequencies can be realized.

Susceptibility to noise is related to signal propagation discussed theoretically above. At higher frequencies the signal propagates shorter distances, thus creating a proximity filter. That is, you only measure what is in proximity to the surface. However, what constitutes proximity will change with frequency and can have important practical ramifications with regard to susceptibility to background noise. Operation at higher frequencies with the mass loading not only results in enhanced signal sensitivity, it also results in lower susceptibility to noise. That can translate functionally to, for example, less stringent washing requirements because the amplifier linked second molecular recognition component that is not bound to the surface of the resonator (e.g., via analyte bound to first molecular recognition component) should not add significant mass in proximity to the surface of the resonator. Furthermore, the washing requirements to obtain a stable baseline reading in negative sample were found to be much less stringent with higher frequency TFBARs, which may also be due to the shorter distance of signal propagation at higher frequency.

Surprisingly, it has been found that larger signal amplification is observed at higher frequencies than at lower frequencies. See, e.g. Table 2 in the EXAMPLES below, where larger signal amplification was observed with enzyme mediated mass loading (relative to direct binding) at 2250 MHz compared with 900 MHz resonators. That larger levels of signal amplification can be obtained at higher frequencies was unexpected because the different resonators (900 MHz and 2250 MHz) were constructed to contain the same concentration or amount of first recognition component, assays used the same concentration and amount of analyte, and the same concentration and amount of enzyme-linked second molecular recognition component and substrate were used. Thus, in theory, the amount of amplification that actually occurs would be expected to be the same (the amount of product precipitated on the surface would be expected the same). However, a larger amount of amplification of signal was observed at higher frequencies.

Use

The sensors, devices and systems described herein may be employed to detect an analyte in a sample. The sensors may find use in numerous chemical, environmental, food safety, or medial applications. By way of example, a sample to be tested may be, or may be derived from blood, serum, plasma, cerebrospinal fluid, saliva, urine, and the like. Other test compositions that are not fluid compositions may be dissolved or suspended in an appropriate solution or solvent for analysis.

Definitions

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. As used herein, "consisting essentially of," as it relates to a composition, product, method or the like, means that the components of the composition, product, method or the like are limited to the enumerated components and any other components that do not materially affect the basic and novel characteristic(s) of the composition, product, method or the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

Any direction referred to herein, such as "top," "bottom," "left," "right," "upper," "lower," and other directions and orientations are described herein for clarity in reference to the figures and are not to be limiting of an actual device or system or use of the device or system. Devices or systems as described herein may be used in a number of directions and orientations.

"Binding event," as used herein, means the binding of a target analyte to a molecular recognition component immobilized in a surface of a sensor.

EXAMPLES

The following non-limiting examples serve to describe more fully the manner of using the above described sensors, methods, devices and systems. It is understood that these examples in no way serve to limit the scope of this disclosure or claims that follow, but rather are presented for illustrative purposes.

Example 1: Enzyme Amplification Proof of Concept

Initial proof of concept studies were performed using an anti-bovine IgG assay and alkaline phosphatase (ALP) as the conjugated enzyme with BCIP/NBT as the precipitating substrate. Briefly, a goat anti-bovine and goat anti-rat antibodies were immobilized on the test and reference resonators by dispensing 350 μm spots using a piezo dispenser onto epoxy silane coated sensors with a resonate frequency of 2.2 GHz. Sensors were incubated overnight in a high humidity environment at 4° C. Sensors were blocked with fish skin gelatin prior to testing. The reference signal was then subtracted from the test signal and this delta signal used as the binding response. All testing performed with the sensors immersed in microtiter plates. Sample agitation achieved by using stirbars. The testing sequence was as follows, sensors were exposed to 1 μg/ml Bovine IgG for 60 seconds followed by a 30 second rinse and exposure to a rabbit anti-bovine IgG-alkaline phosphatase conjugate for 60 seconds. Sensors then rinsed 2 times for 30 seconds and exposed to BCIP/NBT substrate for 60 seconds. Sensors electrically connected to a network analyzer which was used to monitor the frequency shift of the devices. In this case, phase resulting in maximum group delay was tracked and change in input frequency to maintain the phase as mass changed was determined. A 50 MHz window around the resonate frequency was collect at a sampling rate of 2 samples per second for both the test and reference resonators. This data was post processed to determine the frequency shift as a function of time for both the test and reference resonators. The frequency shift observed from direct antigen binding was then compared to the signal observed in the enzyme substrate.

Results of this initial study are presented in FIG. 4A, with FIG. 4B being a detailed view of a portion of the plot presented in FIG. 4A. As shown, the ALP-enzyme amplification resulted in significant improvement in sensitivity relative to direct binding without addition of the substrate.

As shown in Table 1 below, over 100 fold amplification in response and slope was observed as a result of enzyme amplification. P

TABLE 1

Results of ALP-Amplification

| | Direct Binding | Enzyme Amplification |
|---|---|---|
| Response (Integral) | −9,024 | −1,094,473 |
| Amplification (X) | 121 | |
| Slope | −3.24 | −374.77 |
| Slope Amp | 115.71 | |

Similar studies were performed using anti-bovine IgG assay and horse radish peroxidase (HRP) as the conjugated enzyme. The precipitating substrate in this reaction was hydrogen peroxide and p-hydroxycinnamic acid (data not shown). Further analysis on the ALP enhancement with BCIP/NBT using an anti-rat IgG assay was also performed (data not shown). Subsequent development work with the ALP and BCIP/NBT system has included evaluation with a variety of other.

The benefits of precipitate amplification appear to be frequency dependent. Devices with operating frequencies of 2250 MHz and 850 MHz were coated with a Goat anti-Rat F(ab') fragment. The native sulfhydryl group on the reduced F(ab') was used to link to the gold resonator surface forming a dative sulfur gold bond. These sensors were then blocked with fish skin gelatin and tested in negative buffer sample or 1 μg/ml Rat IgG followed by incubation with a goat anti-Rat alkaline phosphatase conjugated antibody. Sensors were then rinsed two times and exposed to BCIP/NBT substrate. Data was reduced as previously described for both the direct binding event and the substrate amplification. Comparison of the 2250 MHz to 900 MHz TFBARs demonstrate a 2.5 fold increase in signal amplification with the higher frequency (2250 MHz) relative to the 850 MHz devices. Additionally, the level of background observed in negative sample was considerably higher in the 850 MHz devices. This was true when the data was analyzed as kHz/sec of response but the difference became even more dramatic when the results were converted to ppm/sec by dividing the frequency shift response by the frequency of operation. The addition of two extra wash steps prior to substrate exposure reduced the amount of background signal in the 850 MHz devices to levels comparable to those seen in the 2250 MHz devices (data not shown).

TABLE 2

Comparison of amplification with 850 and 2250 MHz TFBAR

| Frequency (MHz) | 2250 | 850 |
|---|---|---|
| Background Signal in Negative (ppm/sec) | −0.86 | −23.11 |
| Direct Binding (kHz/sec) | −3.26 | −0.70 |
| Amplified signal (kHz/sec) | −233.7 | −22.3 |
| Amplification (X) | 71.7 | 31.9 |

Example 2: DNA Proof of Feasibility

For DNA binding to the sensors surface a 10 μM 5'-amine labeled 27-mer (complementary to the 3' end of the target oligonucleotide) and 10 μM of a missense 27-mer were both dissolved in 3× saline-sodium citrate (3×SSC) and spotted on epoxy silane functionalized sensors as the test and reference respectively (2150 MHz TFBAR).

A 125-mer oligonucleotide was used as a model target. The target oligonucleotide was mixed with 6 nM of a 3'biotin labeled 18-mer complementary to the 5' end of the 125-mer target in hybridization buffer (5×SSC, 10% formamide, 0.1% SDS) and reacted with the sensor surface for 4 minutes at 39 C.

Figure 7:
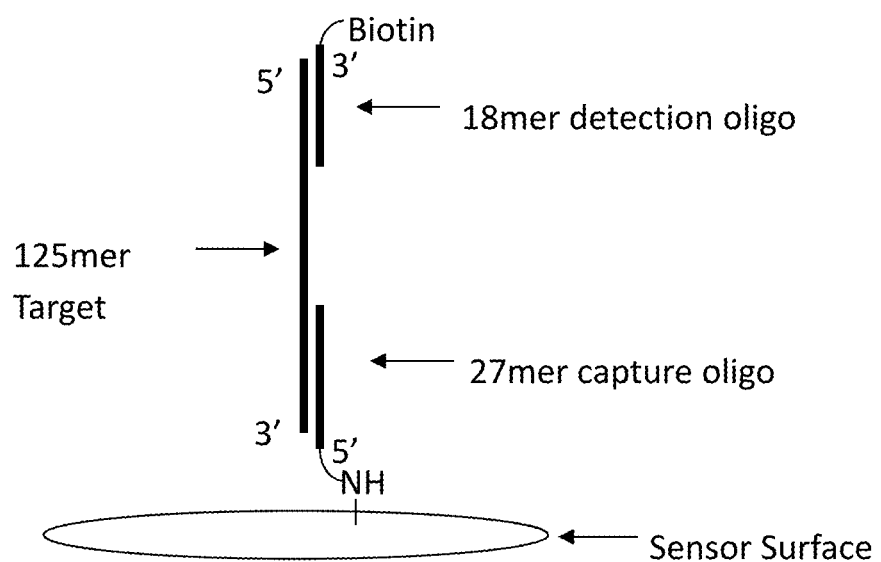
FIG. 7 is a schematic drawing illustrating an embodiment of various polynucleotide components bound to a surface of a TFR as described in EXAMPLE 2.

A schematic diagram of the 27-mer bound to the sensor surface and the target 125-mer, which is bound to the biotinylated 18-mer is shown in FIG. 7.

Two wash steps were then performed (1×SSC with 0.01% SDS and HEPES buffered saline plus detergent) and the sensor was exposed to 2 µg/ml streptavidin-alkaline phosphatase conjugate purchased from Jackson Immuo (Part Number 016-050-084) for 2 minutes in HEPES buffer containing 1 mg/ml fish skin gelatin (FSG).

Two additional wash steps were performed with HEPES plus detergent and the sensor was exposed to the precipitating substrate NBT/BCIP purchased from Thermo (Part Number 34042). Frequency shift data was collected for 1.5 minutes at 39 C and is presented below in Table 3. Estimated limit of detection using the zero response plus 3 standard deviations yielded a value of 0.6 pM.

TABLE 3

Frequency Shift Data

| DNA Target (pM) | Average Response (kHz/sec) |
| --- | --- |
| 0 | 0.93 |
| 0.8 | −0.48 |
| 4 | −2.93 |
| 40 | −38.15 |
| 400 | −111.61 |

Example 3: Interleukin-6 (IL-6) Two-Step Immunoassay

Reagents:

Affinity purified goat anti IL-6 (R&D Systems Part Number AF-206-NA) was spotted onto epoxy silane activated sensors (2175 MHz TFBAR) generally as discussed above for the antibody in EXAMPLE 1.

Mouse monoclonal antibody against IL-6 (R&D Systems Part Number MAB206) was labeled with a 5× molar excess of sulfo-NHS-LC-Biotin (Thermo Scientific) according to the manufacturer's instructions. Excess unincorporated biotin reagent was removed by desalting.

Calibrator matrix was prepared by mixing 10% (v/v) chicken serum (Equitech, charcoal stripped, heat inactivated) with phosphate buffered saline (PBS) plus 0.1% sodium azide. Calibrators were prepared by diluting recombinant human IL-6 (R&D Systems Part Number 206-IL) in Calibrator matrix.

Streptavidin conjugated to alkaline phosphatase (SA-ALP) was purchased from Jackson Immuno (Part Number 016-050-084).

Wash buffer is Hepes buffered saline plus detergent.

Substrate is 1-Step NBT/BCIP purchased from Thermo Scientific (Part Number 34042).

Assay:

Biotinylated mouse anti IL-6 was diluted to a working strength of 8.3 µg/mL in a Hepes buffer containing fish skin gelatin (Hepes/FSG).

SA-ALP was diluted to a working strength of 1 µg/mL in Hepes/FSG.

60 µL of biotinylated mouse anti IL-6 was mixed with 40 µL of calibrator and passed back and forth over the sensor for 16 minutes. The reaction mixture was then removed from the microfluidic channel and SA-ALP was passed back and forth over the sensor for 2 minutes. The sensor was then washed three times with Wash buffer followed by addition of BCIP/NBT substrate. The rate of change in resonance frequency during the substrate step was plotted with respect to IL-6 concentration. The results are shown in the Table 4 below including an estimate of the analytical sensitivity (zero response plus 3 standard deviations).

TABLE 4

Frequency Shift for IL-6 Assay

| IL6 (pg/mL) | Response (kHz/sec) Run | Avg | StDev | CV | Calculated (pg/mL) | Residuals | % Recovery |
| --- | --- | --- | --- | --- | --- | --- | --- |
| 0 | −2.28 | −2.12 | 0.23 | 11% | 0.83 | 0.83 | |
| | −1.96 | | | | <0.83 | NA | NA |
| 5 | −3.53 | −3.48 | 0.08 | 2% | 5.83 | 0.83 | 116.6 |
| | −3.42 | | | | 5.42 | 0.42 | 108.4 |
| 10 | −3.75 | −4.67 | 0.88 | 19% | 6.65 | −3.35 | 66.5 |
| | −4.75 | | | | 10.23 | 0.23 | 102.3 |
| | −5.51 | | | | 12.87 | 2.87 | 128.7 |
| 25 | −8.61 | −9.24 | 0.89 | 10% | 23.32 | −1.68 | 93.28 |
| | −9.87 | | | | 27.48 | 2.48 | 109.92 |
| 100 | −28.49 | −31.44 | 2.77 | 9% | 90.05 | −9.95 | 90.05 |
| | −33.99 | | | | 109.87 | 9.87 | 109.87 |
| | −31.85 | | | | 102.05 | 2.05 | 102.05 |
| 0 + 3SD | −2.82 | analytical sensitivity estimate | | | 3.11 | | |

Thus, embodiments of THIN FILM BULK ACOUSTIC RESONATOR WITH SIGNAL ENHANCEMENT are disclosed. One skilled in the art will appreciate that the leads, devices such as signal generators, systems and methods described herein can be practiced with embodiments other than those disclosed. The disclosed embodiments are presented for purposes of illustration and not limitation. One will also understand that components of the leads depicted and described with regard the figures and embodiments herein may be interchangeable.

What is claimed is:

1. A system for detecting an analyte in a sample, comprising:
   a thin film bulk acoustic resonator (TFBAR) comprising
      a surface to which a first recognition component is immobilized,
         the first recognition component being configured to selectively bind the analyte, an analyte molecule to which a tag is linked, or a tag, or any one of these molecules to which an amplification element-linked second recognition component is bound,
      the TFBAR having a resonance band of about 2 GHz to about 10 GHz;
   one or more containers housing an amplification molecule, the amplification element-linked second recognition component, and optionally one or both of the tag and the analyte molecule;
   a fluid path from the one or more containers to the surface of the TFBAR to which the first recognition component is bound;
   actuation circuitry configured to drive the TFBAR in an oscillating motion;

measurement circuitry arranged to be coupled to the TFBAR and configured to measure one or more resonator output signals representing resonance characteristics of the oscillating motion of the sensing resonator; and a controller operatively coupled with the actuation and measurement circuitry.

2. The system of claim 1, wherein the controller is configured to receive input from the measurement circuitry and determine an oscillation phase shift.

3. The system of claim 2, wherein the oscillation phase shift is an insertion or reflection coefficient phase shift.

4. The system of claim 1, wherein the controller is configured to adjust the actuation circuitry to maintain a resonance point of the TFBAR.

5. The system of claim 4, wherein the resonance point of the TFBAR is a point of maximum group delay.

6. The system of claim 1, wherein the frequency is from about 2 GHz to about 2.5 GHz.

7. The system of claim 1, wherein the amplification element is an enzyme and the amplification precursor is a substrate, and wherein the enzyme is configured to convert the substrate to a precipitate.

8. A kit for use with a device for detecting an analyte in a sample, comprising:
a thin film bulk acoustic resonator (TFBAR) comprising a surface to which a first recognition component is immobilized,
the first recognition component being configured to selectively bind the analyte, an analyte molecule to which a tag is linked, or a tag, or any one of these molecules to which an amplification element-linked second recognition component is bound,
the TFBAR having a resonance band of about 2 GHz to about 10 GHz; and
one or more containers housing an amplification molecule, the amplification element-linked second recognition component, and optionally one or both of the tag and the analyte molecule.

9. The kit of claim 8, further comprising a controller is configured to receive input from measurement circuitry and determine an oscillation phase shift.

10. The kit of claim 9, wherein the oscillation phase shift is an insertion or reflection coefficient phase shift.

11. The kit of claim 9, wherein the controller is configured to adjust actuation circuitry to maintain a resonance point of the TFBAR.

12. The kit of claim 11, wherein the resonance point of the TFBAR is a point of maximum group delay.

13. The kit of claim 8, wherein the frequency is from about 2 GHz to about 2.5 GHz.

14. The kit of claim 8, wherein the amplification element is an enzyme and the amplification precursor is a substrate, and wherein the enzyme is configured to convert the substrate to a precipitate.

* * * * *